(12) United States Patent
Van Liebergen et al.

(10) Patent No.: US 8,535,362 B2
(45) Date of Patent: Sep. 17, 2013

(54) DEVICE FOR CONVEYING AIR TO A PERSON

(75) Inventors: Antonius Josephus Van Liebergen, SC Leusden (NL); Roy Campe, Hoogstraten (BE); Arthur Everardus Officier, GL Epe (NL)

(73) Assignee: The Surgical Company Holding B.V., Amersfoort (NL)

( * ) Notice: Subject to any disclaimer, the term of this patent is extended or adjusted under 35 U.S.C. 154(b) by 1231 days.

(21) Appl. No.: 12/342,933

(22) Filed: Dec. 23, 2008

(65) Prior Publication Data

US 2010/0161012 A1 Jun. 24, 2010

(51) Int. Cl.
*A61F 7/00* (2006.01)

(52) U.S. Cl.
USPC ........... 607/107; 607/104; 607/114; 607/102; 607/103; 607/95; 607/105; 607/106; 607/108; 607/109; 607/110; 607/111

(58) Field of Classification Search
USPC .................................... 604/95, 114, 102–111
See application file for complete search history.

(56) References Cited

U.S. PATENT DOCUMENTS

| | | | | |
|---|---|---|---|---|
| 2,093,834 A * | 9/1937 | Gaugler | ............................ | 4/536 |
| 2,512,559 A * | 6/1950 | Williams | ........................... | 5/502 |
| 3,653,083 A * | 4/1972 | Lapidus | ............................ | 5/713 |
| 4,347,633 A * | 9/1982 | Gammons et al. | ................. | 5/713 |
| 4,572,188 A * | 2/1986 | Augustine et al. | ............ | 607/107 |
| 4,660,388 A * | 4/1987 | Greene, Jr. | ....................... | 62/261 |
| 4,867,230 A * | 9/1989 | Voss | ................................ | 165/46 |
| 5,125,238 A * | 6/1992 | Ragan et al. | ................... | 62/259.3 |
| 5,246,656 A * | 9/1993 | Stephenson et al. | .......... | 264/153 |
| 5,265,599 A | 11/1993 | Stephenson et al. | | |
| 5,304,213 A | 4/1994 | Berke et al. | | |
| 5,342,412 A * | 8/1994 | Ueki | ............................. | 607/114 |
| 5,392,847 A * | 2/1995 | Stephenson | ..................... | 165/46 |
| D359,810 S * | 6/1995 | Namenye | ..................... | D24/206 |
| 5,443,488 A * | 8/1995 | Namenye et al. | ............. | 607/104 |
| D362,507 S * | 9/1995 | Zuck et al. | .................... | D24/206 |
| 5,632,769 A * | 5/1997 | Kappel et al. | ................. | 607/104 |
| 5,640,727 A * | 6/1997 | Kappel | ............................. | 5/482 |
| 5,643,337 A * | 7/1997 | Kappel et al. | ................. | 607/107 |

(Continued)

OTHER PUBLICATIONS

International Search Report (ISR) and Written Opinion (WO) for the International Application No. NL2002367, dated Sep. 24, 2009.

(Continued)

*Primary Examiner* — Nicholas Lucchesi
*Assistant Examiner* — Scott Medway
(74) *Attorney, Agent, or Firm* — Nixon & Vanderhye P.C.

(57) ABSTRACT

The invention relates to a device for conveying heated air to a person and comprises an air-permeable inner sheet and an air-impermeable outer sheet which are connected to one another by welds in order to form a panel-like shape in the inflated state. The welds produce a main duct having, viewed at the inlet end and in the non-inflated state, a main duct width. The main duct is delimited by at least one first series of elongate first welded strips, the first intermediate spaces which are in line with one another. The length of each of these first intermediate spaces, viewed in the non-inflated state, is in each case smaller than the main duct width. The length of each first welded strip is at least 15% of the main duct width and at most 80% of the main duct width.

23 Claims, 5 Drawing Sheets

(56) References Cited

U.S. PATENT DOCUMENTS

| | | | | |
|---|---|---|---|---|
| 5,675,848 A | * | 10/1997 | Kappel | 5/482 |
| 5,683,441 A | * | 11/1997 | Dickerhoff et al. | 607/107 |
| 5,749,109 A | * | 5/1998 | Kappel | 5/423 |
| 5,792,216 A | * | 8/1998 | Kappel | 607/107 |
| 5,890,243 A | * | 4/1999 | Dickerhoff | 5/482 |
| 5,941,907 A | * | 8/1999 | Augustine | 607/104 |
| 6,102,936 A | * | 8/2000 | Augustine et al. | 607/96 |
| 6,371,976 B1 | * | 4/2002 | Vrzalik et al. | 607/104 |
| 6,500,200 B1 | * | 12/2002 | Kushnir | 607/104 |
| 6,709,447 B1 | | 3/2004 | Gammons | |
| 7,291,163 B2 | | 11/2007 | Gammons | |
| 2006/0052851 A1 | | 3/2006 | Anderson et al. | |
| 2006/0135016 A1 | * | 6/2006 | Iwasaki | 442/327 |
| 2008/0288034 A1 | | 11/2008 | Pierre et al. | |
| 2011/0130814 A1 | * | 6/2011 | Nagano et al. | 607/114 |

OTHER PUBLICATIONS

International Search Report (ISR) for PCT/NL2009/050798, mailing date Feb. 25, 2010.

International Preliminary Report on Patentability, Written Opinion, for PCT/NL2009/050798, mailing date Jul. 7, 2011.

* cited by examiner

DEVICE FOR CONVEYING AIR TO A PERSON

BACKGROUND OF THE INVENTION

The present invention relates to a device for conveying air, in particular heated air, to a person, in which the device comprises an air-permeable inner sheet to be turned towards the person and an air-impermeable outer sheet to be turned away from the person; in which the inner sheet and the outer sheet are connected to one another in an air-tight manner by a peripheral weld which, together with the inner and outer sheet, defines an air chamber; in which the device is provided with at least one connection for blowing in air; in which the inner sheet and the outer sheet, in the air chamber, are connected to one another by a plurality of welds in such a manner that, when air is blown into the device via the connection, the former assumes a panel-like shape having a plurality of air ducts which are connected to one another; in which the plurality of ducts comprises a main duct and one or more ancillary ducts; in which the main duct has an inlet end and an outlet end; and in which the connection ends at an inlet end of the main duct.

SUMMARY OF THE INVENTION

A device of this type is known. The Surgical Company markets such devices under the name 'mistral-air'®. Several other companies also market devices of this kind, including Arizant and Mallinckrodt.

Such devices are composed of two sheets, an inner sheet which, in use, is turned towards the person and an outer sheet which, in use, is turned away from the person. The outer sheet is impermeable to air and the inner sheet is permeable to air. This permeability can be achieved in various ways, also in accordance with the present invention, such as by means of an air-tight sheet which is provided with regularly distributed perforations or perforations which are distributed irregularly according to a specific pattern, by means of a sheet which is inherently porous or in another manner. These sheets are connected to one another along the peripheral weld in order to delimit an air chamber between them. Furthermore, a connection is provided for blowing in air. With certain embodiments, two or more of these connections are provided in order to, depending on the application, use one or the other connection. Usually, and preferably also with the present invention, the connections are connections which, prior to use, are closed and, in use, can be opened, for example by removing a sealing film. Thus, no leaks will occur at the connections which are not in use. As is known and also in accordance with the invention, the connections can be arranged in various ways depending on the direction in which the air is blown in, such as essentially transversely to the extending direction of the sheets, obliquely to the extending direction of the sheets or parallel to the extending direction of the sheets.

In use, heated air is blown in between the sheets via the (used) connection and subsequently flows out via the inner sheet in order to maintain the body temperature of the person. Usually, such devices are used before and/or during and/or after a surgical procedure. As a result of air being blown in, the inner and outer sheet will move apart. If the inner and outer sheet in the air chamber were not connected to one another at any further locations, the air being blown in would result in a balloon-shaped convex body. Such a convex body is not suitable for conveying heated air to the person in an evenly distributed manner. In order to achieve this, a relatively flat blanket- or mattress-shaped body (or panel-like shape) is required. This can be produced by connecting the inner and outer sheet to one another by means of a plurality of welds. In this case, the term weld is understood to mean a connection between the inner and outer sheet which limits the distance between the inner and outer sheet at the location of this connection to a maximum value.

According to the invention, a weld will usually be a direct connection between the inner and outer sheet (in which case the sheets will be stuck to one another in that location), but can also be an indirect connection via an intermediate element. According to the invention, a weld can furthermore be produced by a variety of connection techniques, such as by means of an adhesive or by means of a heat seal.

A problem which occurs with such prior-art devices is that the temperature of the air emerging from the inner layer may differ widely between the various discharge locations. Differences in temperature of 5 to 8° C. between different locations are a regular occurrence. This is undesirable and is caused by the poor distribution of air blown in across the air chamber.

It is an object of the present invention to provide an improved device of the type mentioned in the preamble of claim 1 which, on the one hand, improves the distribution of air blown in across the air chamber and, on the other hand, ensures that it is inflated correctly to produce the desired shape.

According to the invention, this object is achieved by providing a device for conveying heated air to a person,
in which the device comprises an air-permeable inner sheet to be turned towards the person and an air-impermeable outer sheet to be turned away from the person;
in which the inner sheet and the outer sheet are connected to one another in an air-tight manner by a peripheral weld which, together with the inner and outer sheet, defines an air chamber;
in which the device is provided with at least one connection for blowing in air;
in which the inner sheet and the outer sheet, in the air chamber, are connected to one another by a plurality of welds in such a manner that, when air is blown into the device via the connection, the former assumes a panel-like shape having a plurality of air ducts which are connected to one another;
in which the plurality of ducts comprises a main duct and one or more ancillary ducts;
in which the main duct has an inlet end and an outlet end;
in which the connection ends at an inlet end of the main duct;
which device according to the invention is characterized by the fact that the main duct, viewed at the inlet end and in the non-inflated state, has a main duct width;
the plurality of welds comprises at least one first series of elongate first welded strips, the first intermediate spaces between which are in line with one another, which first series delimits one side of the main duct;
the length of each of these first intermediate spaces, viewed in the non-inflated state, is in each case smaller than the main duct width;
the length of each first welded strip of the first series is at least 15% of the main duct width; and
the plurality of welds comprises a dividing weld which is arranged at the outlet end in line with the main duct.

According to the invention, the width of the main duct, also referred to as main duct width, is measured at the start of the duct, i.e. the inlet, and at right angles to the welded strip situated at the inlet.

In this case, the dividing weld is designed to divide an air flow emanating from the main duct into two parting air flows. The Applicant has found that once a device of the type according to the preamble of claim 1 has been inflated, the resulting ducts and ancillary ducts are maintained during further use-provided air is being blown in (and therefore retain their shape). The dimensions of the device according to the preamble of claim 1 will be reduced while it is being inflated, viewed transversely to the longitudinal direction of the main duct/the ancillary ducts, as a result of the sheets bulging at the location of the main duct/the ancillary ducts. The Applicant has found that, in this case, once a main duct has formed in a device of the type according to the preamble of claim 1, no further ducts will form which are transverse thereto and that it is therefore possible to impose the (desired) direction of the main duct and the ancillary ducts beforehand (dimensional reliability). Since the lengths of the first intermediate spaces are smaller than the main duct width and since, at the same time, the length of each first welded strip of the first series is at least 15% of the main duct width (i.e. at a main duct width of, for example, 180 mm, the length of the first welded strip will be at least 27 mm), it is ensured that when air is blown in, the main duct on the one hand is inflated first (dimensional reliability) and on the other hand remains inflated (dimensional stability). The flow passage through the main duct is larger than that of the first intermediate spaces which, together with the lengths of the first welded strips of the first series ensures a dimensionally reliable and dimensionally stable main duct, so that the rest of the air chamber can quickly be fed from the main duct, in which the first intermediate spaces allow the lateral flow of air from the main duct to adjacent sections of the air chamber for a quick and even distribution of air blown in across the air chamber, which results in an even temperature of the air flowing from the inner sheet along the person. The dividing weld which divides the air flow emanating from the main duct into two parting air flows ensures that the air which emanates from the main duct flows away to the sides in an efficient manner, resulting in the air quickly reaching other locations in the air chamber and a pressure being built up downstream of the outlet end, which leads to an even distribution of air across the surface of the inner sheet. This contributes greatly to reducing temperature differences (of the air flowing out of the inner sheet) between different locations on the inner sheet.

According to a further embodiment of the device according to the invention, further welded strips are provided on that side of the dividing weld which, viewed in the direction of flow of the main duct, is downstream and these further welded strips define one or more further ducts which extend to that end of the air chamber which is situated on said downstream side of the dividing weld. These further ducts result in an efficient supply of air of that section of the air chamber which is situated downstream of the dividing weld, so that here the air emanating from the inner sheet also has a temperature which does not deviate, or hardly deviates at all, from that of the air which emanates from the inner sheet elsewhere.

According to a further embodiment of the invention, it is advantageous if the distance from the dividing weld to the outlet end of the main duct is 50% to 100% of the diameter of the main duct in the inflated state, said diameter of the main duct in the inflated state being defined as: $2 \times A/\pi$, with A=the main duct width in the non-inflated state. Preferably, the dividing weld is in this case provided substantially in line with the longitudinal axis of the main duct. Thus, at the end of the main duct, the lateral (with respect to the main direction of the main duct) passage for the flow of air will be approximately equal in size in both directions and, when added up for both directions, will be approximately equal in size to the cross section of the main duct.

According to a further embodiment of the invention, the length of each first welded strip of the first series is at least 20% of the main duct width (in the non-inflated state). Thus, the dimensional stability and dimensional reliability of the main duct is ensured further.

According to yet a further embodiment of the invention, the length of each first welded strip of the first series is at most 70%, such as at most 60%, of the main duct width (in the non-inflated state). Thus, the feeding of the air chamber laterally from the main duct in an evenly distributed manner is further improved.

According to yet a further embodiment of the invention, the length of the first intermediate space between the first welded strips of the first series is at most 80% of the main duct width (in the non-inflated state), preferably at most 75% of the main duct width (in the non-inflated state), more preferably at most 70% of the main duct width (in the non-inflated state). Thus, the dimensional stability of the main duct and of the entire device in the inflated state is further improved.

According to yet a further embodiment of the invention, the length of the first intermediate space between first welded strips of the first series is at least 50% of the main duct width (in the non-inflated state), preferably at least 60% of the main duct width (in the non-inflated state). In this way, quick feeding of those sections of the air chamber which are situated to the side of the main duct is ensured.

In one embodiment in which the air chamber has an elongate shape and in which the connection is provided at a transverse side of the elongate shape, in the centre thereof, it is furthermore advantageous according to the invention if the main duct is a straight duct which is delimited on both sides by said first series of first welded strips; and if at least one first ancillary duct runs on either side of the main duct and parallel to the main duct. Thus, a quick and efficient supply from the main duct to the air chamber is achieved. For feeding both sides of the main duct evenly, it is in this case advantageous if the first welded strips of the first series in each case are of an approximately equal length and if the first intermediate spaces in each case have an approximately equal length.

With this embodiment, it is furthermore advantageous if the plurality of welds, at the outlet end, has a first elongate connecting weld in line with each first series and at a distance thereto, which first connecting welds, viewed in the direction of flow of the main duct, diverge from one another and have a length which is longer than that of the first welded strips of the first series. Thus, the quick and even feeding of the transverse side of the air chamber which is turned away from the connection is improved.

In the case of relatively wide air chambers, it is advantageous with this embodiment if a second ancillary duct extends along that side of each first ancillary duct which is turned away from the main duct; if the plurality of welds comprises a second series of elongate second welded strips on each side of the main duct which are in line with second intermediate spaces and form the partition between the first and second ancillary duct; and if the length of each of these second intermediate spaces, viewed in the non-inflated state, is in each case greater than the length of the first intermediate spaces. Thus, an efficient supply from the first ancillary ducts to the second ancillary ducts is achieved. It is in this case furthermore advantageous if, viewed in the non-inflated state, the length of the second intermediate spaces is greater than 80%, in particular greater than 90%, of the width of the first ancillary duct. The result of this is that air which arrives in the first ancillary duct is preferred to flow down to the second ancillary duct, in addition to flowing out of the inner sheet from the first ancillary duct. In order to achieve and maintain the desired shape of the inflated air chamber, it is in this case advantageous if the length of each second welded strip of the second series is 30% to 70%, for example 40% to 60%, of the length of the first welded strips of the first series. For an even distribution of air along both longitudinal sides of the air chamber, it is in this case advantageous if the second welded strips of the second series are of approximately equal length; and if the second intermediate spaces in each case are of approximately equal length. The quick and even feeding of the transverse side of the air chamber which is turned away from the connection is improved in this case, if the plurality of welds, at the outlet end, in line with each second series and at a distance therefrom has an elongate second connecting weld, which second connecting welds, viewed in the direction of flow of the main duct, diverge from one another and have a length which is greater than that of the first welded strips of the first series.

For a quick distribution of air supplied to the inlet end of the main duct, it is advantageous according to the invention if the plurality of welds, at the inlet end, in line with each first and, if present, second series comprises a third connecting weld, which is in particular pointed. It is in this case furthermore advantageous if the connection outside the main duct is provided upstream of the inlet thereof and is designed in such a manner that the supply direction of the air is transverse to the outer sheet.

According to another embodiment, in which the air chamber has an elongate shape; and in which the connection is provided on a longitudinal side of the elongate form, it is advantageous according to the invention if the main duct is a curved duct which extends from the connection to the centre of said air chamber, viewed in the width direction of the elongate air chamber; if the first series delimits the inner-bend side of the main duct; if a third ancillary duct extends on the outer-bend side of the main duct which is substantially straight and extends in the longitudinal direction of the elongate air chamber; if the plurality of welds comprises a third series of elongate third welded strips which are in line with third intermediate spaces, which third series delimits that side of the third ancillary duct which is adjacent to the main duct; and if the plurality of welds comprises one or more outer-bend welded strips which are directed obliquely towards the third series in order, together with one or more third welded strips of the third series which are situated downstream of the outer-bend welded strips, to form the outer bend of the main duct. This other embodiment is inter alia required when air is to be conveyed to the upper body of a person with one or both arms extended in the transverse direction of the body of the person. In practice, it has been found that it is desirable in this case for the connection to be situated on a longitudinal side. By designing the main duct in the form of a curve extending from the connection to the transverse centre of the air chamber, with the inner-bend side turned away from the longitudinal centre of the air chamber and designed as first series, and providing a third ancillary duct in the longitudinal direction of the air chamber, the boundary of which meets the outer-bend boundary of the main duct, a quick and even distribution of supplied air across the air chamber can be achieved despite said substantially unfavourable positioning of the connection.

In order to further improve the quick and even distribution of supplied air across the air chamber, it is advantageous in the case of this other embodiment if a fourth ancillary duct extends on that side of the third ancillary duct which is turned away from the main duct, and extends parallel to the third ancillary duct; if the plurality of welds comprises a fourth series of elongate fourth welded strips which are in line with fourth intermediate spaces, which fourth series forms the boundary between the third and fourth ancillary ducts; and if the length of each of these fourth intermediate spaces, viewed in the non-inflated state, is in each case greater than the length of the first intermediate spaces.

In the case of this further embodiment, it is advantageous, for a quick and even distribution of supplied air along the transverse side of the air chamber which is situated opposite the inlet of the main duct, if the one or more ancillary ducts have a first end and if, viewed in the transverse direction of the elongate chamber, these first ends are situated substantially next to the inlet end of the main duct; and if, viewed in the longitudinal direction of the elongate air chamber, the plurality of welds upstream of the inlet end comprises one or more fourth connecting welds.

If this other embodiment is intended for conveying air to the upper body of a person with both arms in the transverse direction of the body of the person, it is advantageous according to the invention if the elongate air chamber, viewed in the longitudinal direction thereof, has a longitudinal centre and is mirror-symmetrical with respect to a mirror axis which is at right angles to the longitudinal axis of the elongate air chamber and crosses this longitudinal centre. Thus, a universal device is produced which, in use and depending on preference, offers the choice of supplying the air via the connection on the left-hand or right-hand side of the person. For an efficient distribution of the air supplied, it is in this case particularly advantageous if the connections are provided at approximately one quarter and three quarters of the length of the elongate chamber.

According to the invention, it is furthermore advantageous if the inner sheet has an evenly distributed permeability to air of <300 mm/sec, in particular ≦200 mm/sec, measured according to ISO 9237:1995(E). This standard defines the permeability to air as: "Velocity of an air flow which passes through a test specimen at right angles under specified conditions of the test environment, pressure drop and time". The specified conditions, measuring procedure, etc. can be found in said ISO 9237:1995(E). The permeability to air of <300 mm/sec, in particular ≦200 mm/sec, results in a low velocity of air coming from the inner sheet, which counteracts any draught effects when this air flows along the body of the person. These low permeability values are possible in particular with the method of producing the plurality of welds according to the invention without this being to the detriment of an even temperature (that is to say that the temperature is approximately equal at each location of the inner sheet) of the air flowing out of the inner sheet.

According to a further embodiment of the device according to the invention, the sections of the inner sheet and outer sheet which are situated inside the peripheral weld, viewed in the length and width direction of these sheets, have substantially identical dimensions, in which the inner sheet and outer sheet, viewed in the non-inflated state, substantially lie against one another by those sides of said sheets which are turned towards one another.

It should be noted that a welded strip according to the invention may not only have an elongate rectangular or elongate oval shape, but that it can also be composed of a series of spot welds which are close together.

SHORT DESCRIPTION OF THE FIGURES

The present invention will be described below in more detail with reference to two embodiments illustrated in the attached drawing, in which.

DESCRIPTION OF EMBODIMENTS

Figure 7:
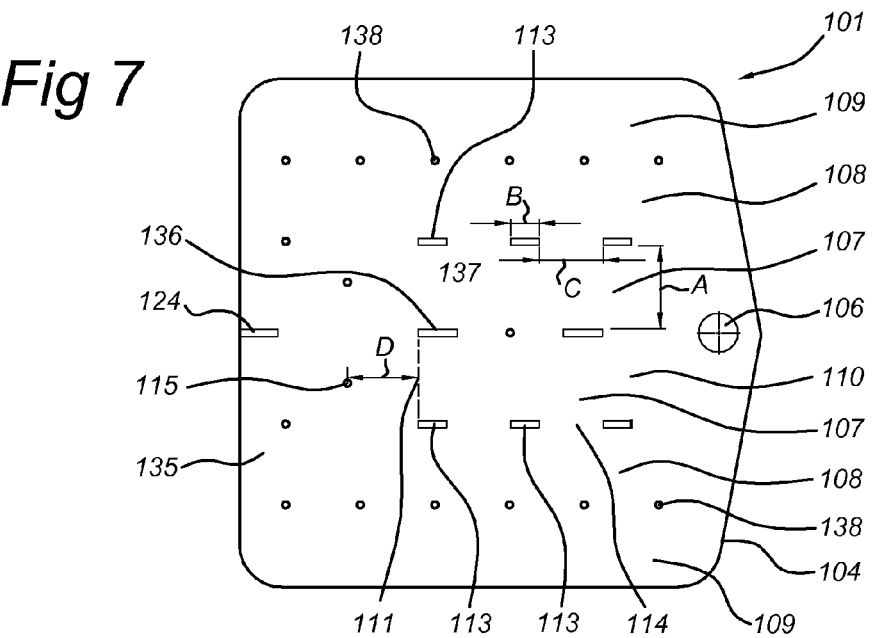
FIG. 7 shows a diagrammatic top view of yet a third embodiment of the invention.
Figure 8:
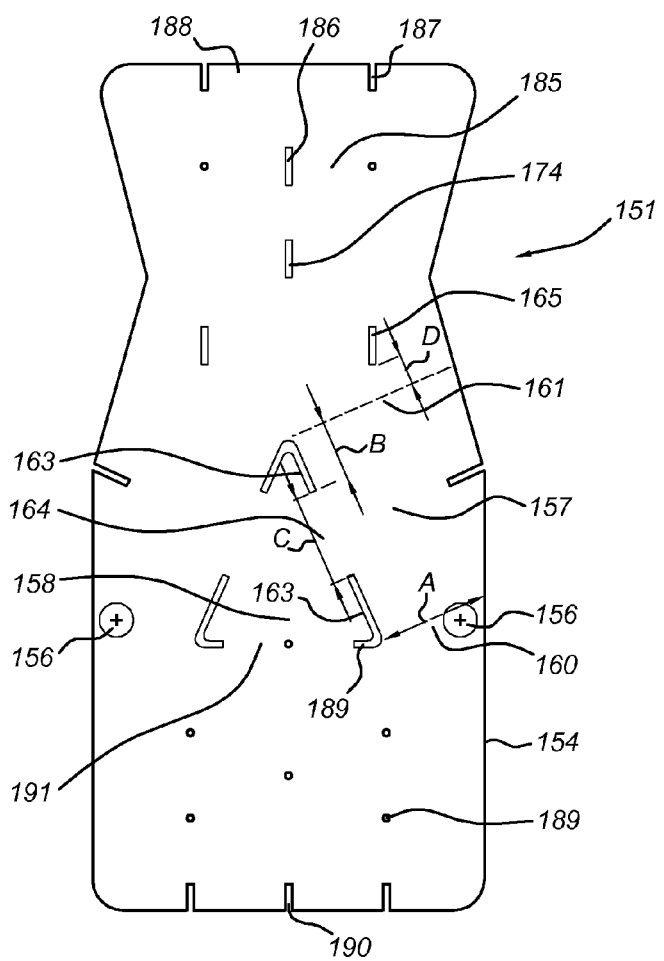
FIG. 8 shows a diagrammatic top view of yet a fourth embodiment of the invention.

As is known in this field, there are different methods and areas of application, depending on which the Applicant uses various designations for models in its range according to the prior art (as do competitors), such as model 'adult' (the embodiment according to FIGS. 1-4), model 'upper body' (FIGS. 5-6); model 'paediatric' (FIG. 7); and model 'half upper body' (FIG. 8). Other embodiments are also possible. The present invention is therefore not limited to the four embodiments described in the present document. The scope of the present invention is thus defined by the claims and not by the embodiments illustrated in the drawing.

In FIGS. 1-4, the first discussed embodiment of the device according to the invention, model 'adult', is denoted by reference numeral 1. Said device 1 is composed of an inner sheet 2 and an outer sheet 3. In use, the inner sheet is turned towards the person 100 and the outer sheet 3, in use, is turned away from the person 100. Both sheets 2 and 3 are connected to one another in an air-tight manner along a peripheral weld 4 so that an air chamber 5 forms between the sheets 2 and 3 and the peripheral weld 4. In use, air can be blown into this air chamber 5 via a connection 6. As a result of the outer sheet 3 being air-tight and the inner sheet 2 being air-permeable, this air blown in will then flow out of the inner sheet and flow along the person. Usually, the supplied air will be heated air at a temperature from ambient temperature up to approximately 45° C. As a result of interim cooling, the air emanating from the bottom sheet will have a slightly lower temperature, but will as far as possible be even across the exterior of the bottom sheet. If desired, the supplied air may also be cooler than 40°, for example lower than body temperature. The user will be able to vary the temperature of the supplied air as desired. Taking into account the interim cooling, the temperature of the supplied air will determine the temperature of the air emanating from the inner sheet 2.

Figure 1:
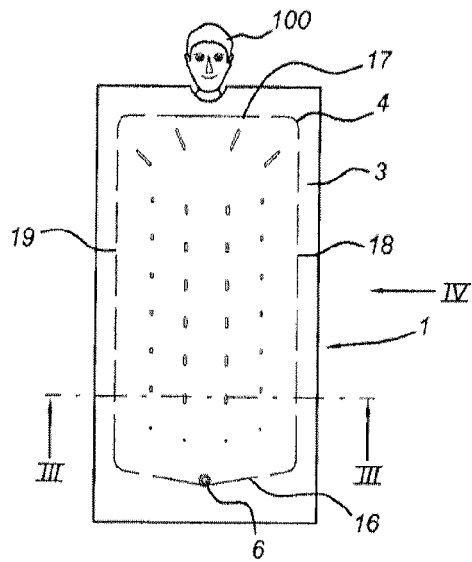
FIG. 1 shows a diagrammatic top view of a first embodiment of the invention.
Figure 2:
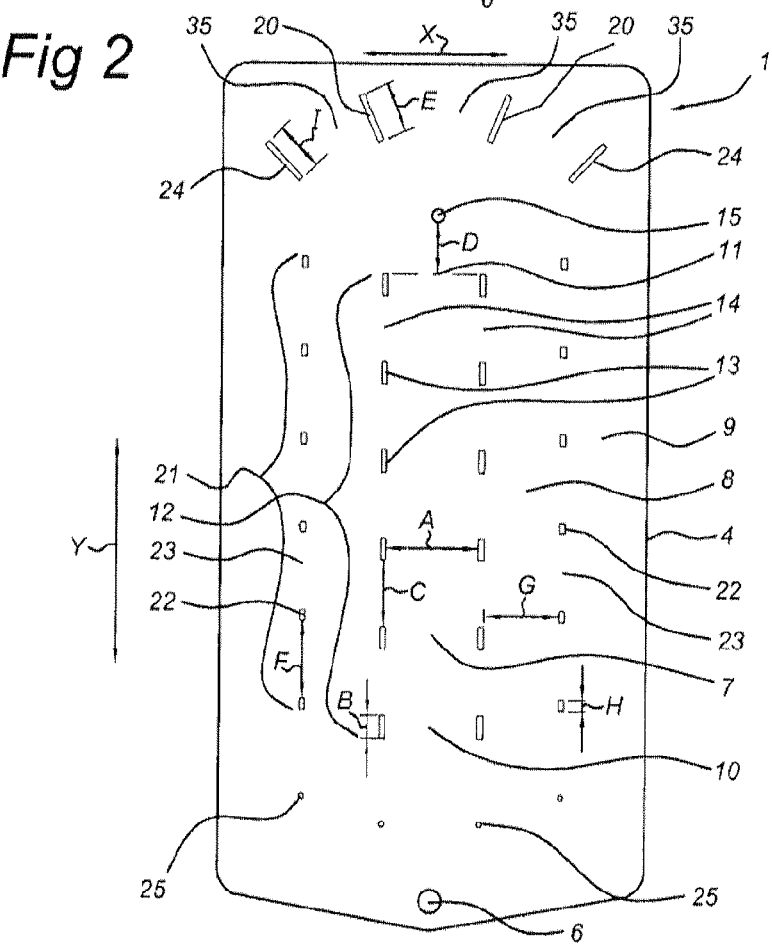
FIG. 2 shows a diagrammatic view corresponding to FIG. 1, which shows the configuration of the welds in more detail.
Figure 3:
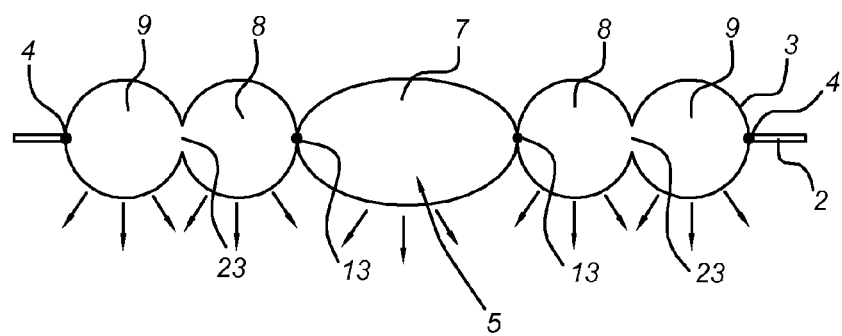
FIG. 3 shows a cross-sectional view along arrows III-III in FIG. 1.
Figure 4:
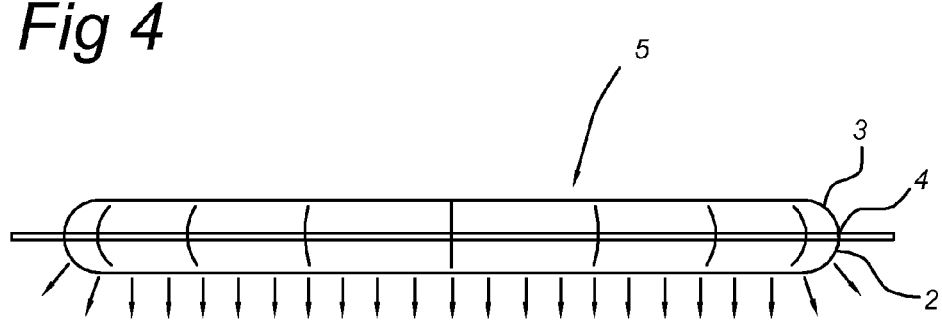
FIG. 4 shows a longitudinal side view along arrow IV from FIG. 1.

As can be seen in the cross section from FIG. 3 and the view from FIG. 4, in the inflated state, the device 1 according to the invention assumes a panel-like shape, resembling a mattress or blanket, as it were. This panel-like shape is achieved by the fact that the inner sheet 2 and outer sheet 3 are not only connected to one another along the peripheral weld 4, but also in between, inside the air chamber 5 itself.

The device according to FIGS. 1-4 has an elongate air chamber 5 with short transverse sides 16 and 17 and long longitudinal sides 18 and 19. The connection 6 is provided in the centre of the transverse side 16. In the centre of the air chamber, between sheets 2 and 3, a main duct 7 is formed which has a first ancillary duct 8 and a second ancillary duct 9 on either side. The main duct 7 and the ancillary ducts 8 and 9 start at a distance from transverse side 16, end at a distance from transverse side 17 and run parallel to longitudinal sides 18 and 19.

The main duct 7 is delimited on either side by a first series 12 of first welded strips 13 with first intermediate spaces 14 in between and has an inlet end 10 and outlet end 11. At a distance downstream of the outlet end 11 of the main duct, a dividing weld 15 is provided in line with the longitudinal axis of the main duct 7. The connection 6 is provided in line with the longitudinal axis of the main duct 7 at a distance upstream of the main duct.

On the side of the main duct 7, the first ancillary duct 8 is delimited by the first series 12 of first welded strips 13. On the other side, the first ancillary duct is delimited by a second series 21 of welded strips 22 which are spaced apart by second intermediate spaces 23.

On the transverse side 17, downstream from dividing weld 15, further welded strips 20, 24 are provided, in this case referred to as first connecting welds 20 and second connecting welds 24. First connecting welds 20 are in line with the first series 12 of first welded strips 13 and second connecting welds 24 are in line with the second series 21 of second welded strips 22. More important than the arrangement of the connecting welds in line with the first and second series 12, 21 (this arrangement could also be different) is the fact that these connecting welds 20, 24 are elongate and delimit further ducts 35 between them. The connecting welds 20, 24 and the further ducts 35 are provided in a fan pattern. The elongate shape and the fan pattern ensure that a) the air emanating from the outlet end 11 of the main duct and from the outlet ends of the ancillary ducts 8 and 9 is conveyed quickly and efficiently as far as the outer position on the transverse side 17 and that b), in the inflated state, the total width of the device in the width direction X on transverse side 17 is equal to the total width of the device at the main duct 7 and the ancillary ducts 8 and 9.

On transverse side 16, upstream of the inlet end 10 of the main duct 7 and the inlets of the ancillary ducts 8 and 9, third connecting welds 25 are provided which are designed, in particular, as pointed or circular welds. These third connecting welds 25 serve to keep the inner and outer sheets 2, 3 together, so that the latter, in the inflated state, do not become substantially more convex than at the location of the main duct and the ancillary ducts, while, at the same time, the supplied air can be distributed quickly and efficiently across the width of the device on transverse side 16 in order to feed main duct 7 and ancillary ducts 8, 9.

The connection 6 is attached at right angles to the outer sheet 3 in order to supply the air in a direction transverse to the outer sheet 3. Since no partition or other obstruction is provided between the connection 6 and the inner sheet 2, this supplied air will hit the inner sheet 2 at right angles or at an angle, if the connection is in an oblique position with respect to the inner sheet 2 as a result of the flexibility of the outer sheet 3.

When air is supplied via the connection 6, it will distribute in the width direction X on the transverse side 16 and will mainly feed the main duct 7 during the initial phase of inflating. From the main duct 7, the ancillary ducts 8 will subsequently be fed via the first intermediate spaces 14 and, from the ancillary ducts 8, the ancillary ducts 9 will be fed via the intermediate spaces 23. As soon as air leaves the outlet end 11 of the main duct 7, it will be deflected into two lateral deflecting flows by the dividing weld 15. As soon as the unit is inflated, the main duct 7 will start to operate as a distributing element to provide an even supply to the entire air chamber.

As an indication for the device 1 according to FIGS. 1-4, the following dimensions may be mentioned by way of example:

first welded strip 13: 40 mm (length B)×10 mm (width);
length C of first intermediate space 14: 120 mm;
width A of main duct (=main duct width): 180 mm;
second welded strip 22: 20 mm (length E)×10 mm (width);
length F of second intermediate space 23: 140 mm;
width G of first ancillary duct 8: 150 mm;
width of second ancillary duct 9: 160 mm;
second connecting weld 20: width 10 mm, length E 90 mm, at an angle of 22.5° with respect to the longitudinal axis of the main duct, the end turned towards the transverse side 17 at 139 mm from the longitudinal axis of the main duct and at 60 mm from the transverse side 17;
third connecting weld 24: width 10 mm, length I 90 mm, at an angle of 45° with respect to the longitudinal axis of the main duct, the end turned towards the transverse side 17 at 316 mm from the longitudinal axis of the main duct and at 150 mm from the transverse side 17;
first series 12 with last welded strip ending at 380 mm from the transverse side 17;
second series 23 with last welded strip ending at 350 mm from the transverse side 17;
dividing weld 15: at 290 mm from transverse side 17 and circular with a diameter of 10 mm;
third connecting welds 25: in each case at 155 mm directly in line with the respective series and circular with a diameter of 10 mm.

Figure 5:
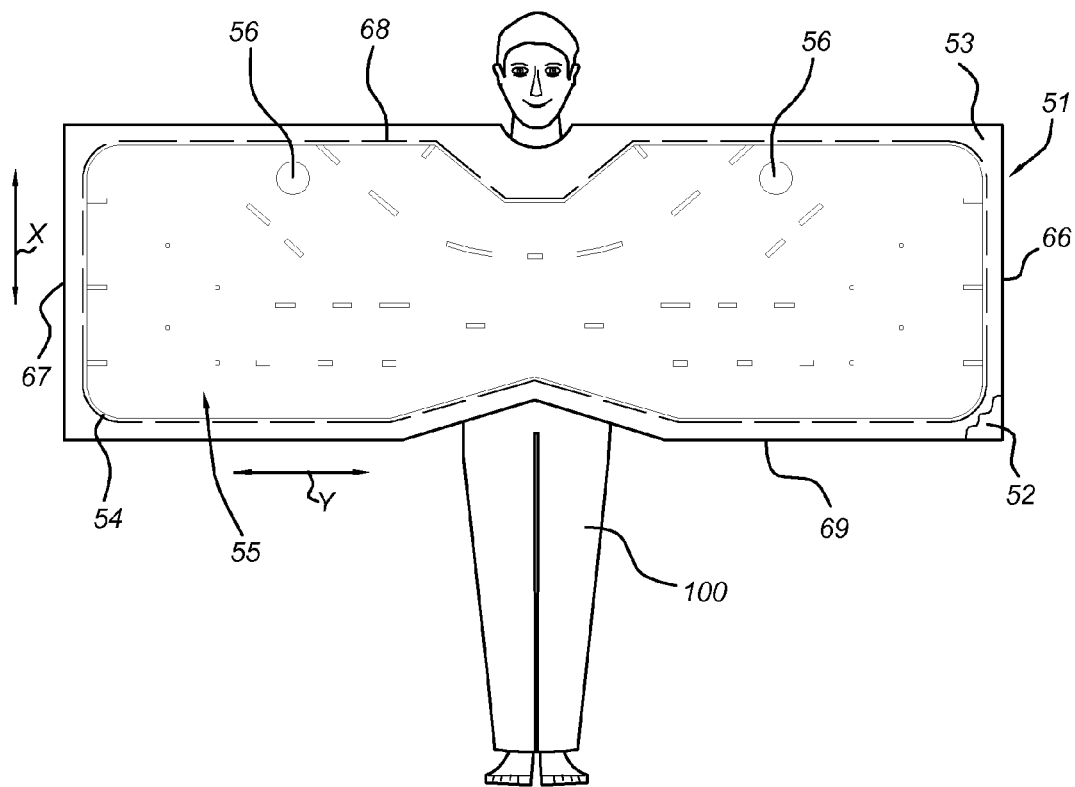
FIG. 5 shows a diagrammatic top view of a second embodiment of the invention.
Figure 6:
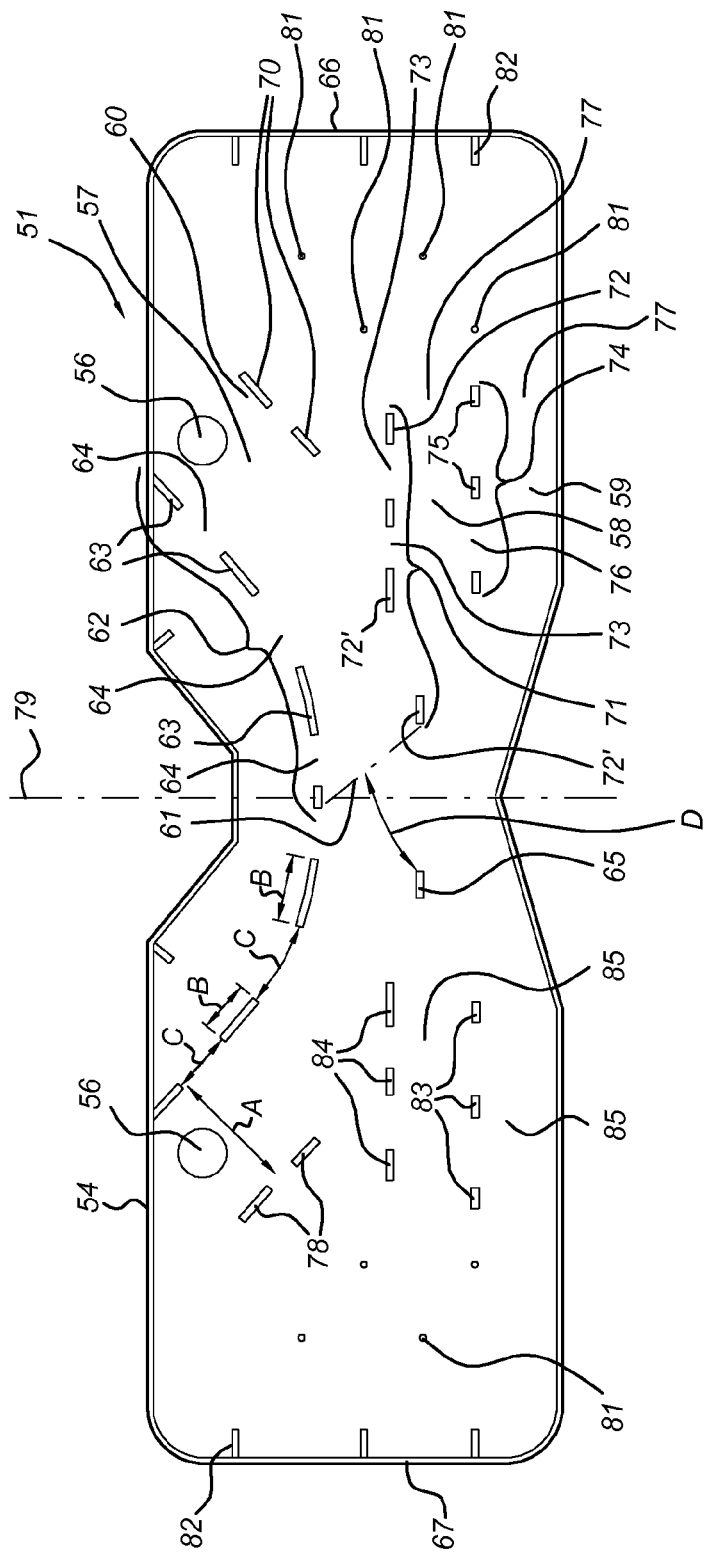
FIG. 6 shows a diagrammatic view corresponding to FIG. 5, which shows the configuration of the welds in more detail.

In FIGS. 5-6, the second discussed embodiment of the device according to the invention is denoted by reference numeral 51, model 'upper body'. This device 51 is composed of an outer sheet 53 and an inner sheet 52 (made visible in FIG. 5 by the fact that part of the outer sheet 53 has been removed at a corner). In use, the inner sheet is turned towards the person 100 and the outer sheet is, in use, turned away from the person 100. Both sheets 52 and 53 are connected to one another along a peripheral weld 54 in an air-tight manner, so that an air chamber 55 forms between the sheets 52 and 53 and the peripheral weld 54. In use, air can be blown into this air chamber 55 via one of the connections 56, as desired. Because the outer sheet 53 is air-tight and the inner sheet 52 is air-permeable, the air blown in will then also emerge from the inner sheet and flow along the person. What has been said with reference to FIGS. 1-4 with regard to the temperature of the air blown in and the temperature of the air emanating via the inner sheet applies here as well.

As with the other embodiment illustrated in FIGS. 3-4, the device 51 according to the invention also assumes a panel-like shape in the inflated state, resembling a mattress or blanket, as it were. This panel-like shape is achieved by the inner sheet 52 and outer sheet 53 not only being connected to one another along the peripheral weld 54, but also in between, in the air chamber 55 itself. However, because the position of the connection 56 is different here, the pattern of the plurality of welds differs.

The device from FIGS. 5-6 has an elongate air chamber 55 with short transverse sides 66 and 67 and long longitudinal sides 68 and 99. Two connections 56 are provided on longitudinal side 68. Viewed in the length direction Y, these connections are at approximately ¼ and ¾ of the length of the elongate air chamber 55. The elongate air chamber 55 is designed to be symmetrical with respect to the mirror axis 79 in order to be able to select one connection 56 or the other connection 56 for the supply of air, depending on circumstances.

The following description is given based on the assumption that the connection 56 which is on the right-hand side in FIGS. 5-6 is used for the supply of air. Furthermore, it is pointed out that the terms 'third' and 'fourth' will be used to denote parts, while the term 'second' and occasionally also the term 'first' with regard to the same part do not occur in the description of this embodiment. This has been done in order to prevent confusion with parts of the embodiment according to FIGS. 1-4. In those instances where the terms 'first', 'second', 'third', 'fourth', etc. are used in this patent application, this has only been done in order to be able to distinguish the various parts in the text and this numbering does not give any indication as to whether parts are present which have higher or lower numbers.

Between the sheets 52 and 53, a curved main duct 57 is formed. Next to the main duct, the third ancillary duct 58 extends, and next to that the fourth ancillary duct 59.

The inner-bend side of the main duct 57 is formed by a first series 62 of welded strips 63 which are arranged in line with one another with intermediate spaces 64 between them. The outer bend side of the main duct 57 is delimited by outer-bend welded strips 70 and the welded strips 72', which form part of a third series 71 of third welded strips 72, 72'. The third series of welded strips 72, 72' forms the boundary of the third ancillary duct 57 which is turned towards the main duct. On the other side, the third ancillary duct 58 is delimited by the fourth series 74 of fourth welded strips 75 which are provided with fourth intermediate spaces 76 between them.

The main duct 57 and the ancillary ducts 58 and 59 start at a distance from transverse side 66 and end at a distance from transverse side 67. The ancillary ducts 58 and 59 extend parallel to longitudinal sides 68 and 69.

In line with the main duct 57, a dividing weld 65 is provided at a distance D downstream from the outlet end 61 of the main duct 57. The connection 56 is provided in the inlet end 60 of the main duct 57.

Downstream of dividing weld 65, further welded strips 78, 83 and 84 are provided which delimit further ducts 85. These further ducts ensure that the air downstream (in this case to the left) of the dividing weld 65 are passed to the left-hand transverse side 67 of the air chamber 55 in an efficient manner.

On the transverse side 66, to the right of the inlet end 60 of the main duct 57 and the right-hand ends of the ancillary ducts 58 and 59, fourth connecting welds 81 are provided, which are designed in particular as pointed or circular welds. These fourth connecting welds 81 serve to keep the inner and outer sheets 52, 53 together, so that the latter, in the inflated state, do not become substantially more convex that at the location of the main duct and the ancillary ducts, while, at the same time, the supplied air can be distributed quickly and efficiently across the width of the device on transverse side 66.

The connection 56 is attached at right angles to the outer sheet 53 in order to supply the air in a direction transverse to the outer sheet 53. Since no partition or other obstruction is provided between the connection 56 and the inner sheet 52, this supplied air will hit the inner sheet 52 at right angles or at an angle, if the connection is in an oblique position with respect to the inner sheet 52 as a result of the flexibility of the outer sheet 53.

When air is supplied through the right-hand connection 56, this will initially fill the main duct 57 on the—viewed with respect to the symmetry axis 79—right-hand half and subsequently the main duct 57 on the left-hand half, thus ensuring dimensional reliability. Thereafter, the ancillary ducts 58, 59 and the rest of the air chamber 55 will then be filled and fed. As soon as air leaves the outlet end 61 of the main duct 57, this will be deflected into two lateral deflected flows by the dividing weld 65, the one flow continuing in the main duct 57 on the left-hand half and the other flow passing to the ancillary ducts 58, 59 on the left-hand half. As soon as the entire unit is inflated, the portion of the main duct 57 which is situated on the right-hand and left-hand half will start to act as a distributing element for supplying the entire air chamber 55 in an even manner.

It should be noted that the device from FIGS. 5 and 6 is designed to be mirror-symmetrical with respect to the mirror axis 79. The above description is based on air being blown into the right-hand connection 56 (with the left-hand connection remaining closed). In order to be able to functionally distinguish the welds on the right-hand side of the mirror axis 79 from the welds on the left-hand side of the mirror axis when air is being blown in from the right-hand side, different reference numerals have been used for corresponding welds to the right and left of the mirror axis, for example the welds 75 to the right are identical to the welds 83 on the left, but they do not function in exactly the same way. It will be clear that when air is blown in from the left-hand connection 56, while the right-hand connection 56 remains closed, the reference numerals can also be mirrored with respect to the mirror axis, as a result of which the above description can be followed again.

As an indication for the device 51 according to FIGS. 5-6, the following dimensions may be mentioned by way of example:

- first welded strips 63: different length dimensions from inlet end 60 to outlet end 61 successively: length 60 mm, 74 mm, 100 mm and 30 mm; the width in each case remains equal at 10 mm;
- outer-bend welded strips 70: width of both 10 mm; length different, from inlet end 60 to outlet end 61 successively 60 mm and 50 mm;
- dividing weld 65: length 40 mm and width 10 mm
- third welded strips 72 from third series: width of both 10 mm and length 40 mm;
- third welded strips 72' from third series: width of both 10 mm and different lengths of 60 mm and 40 mm respectively.
- fourth welded strips 75: all with width 10 mm and length 30 mm;
- fourth connecting welds 81: circular with a diameter of 10 mm;
- transverse side welds 82: length 40 mm and width 10 mm;
- width A of main duct (main duct width) at inlet end: 180 mm
- length C of first intermediate space: different, from inlet end 60 to outlet end 61 successively 90 mm, 110 mm, 70 mm;
- other dimensions can be determined from FIG. 6 by approximation, using scaling factors which can be deducted from the above dimensions.

FIG. 7 shows the third embodiment, model 'paediatric', which is generally denoted by reference numeral 101. It is composed of an inner sheet which is permeable to air and an outer sheet which is impermeable to air is, both sheets being connected to one another by a peripheral weld 104 in order to define an air chamber between them, and a connection 106 is provided in the outer sheet for blowing in air. It has two main ducts 107, which are separated from one another by two welded strips 136 and a spot weld 137. The connection 106 is in line with the welded strips 136 at some distance in front of the inlets 110 of both main ducts 107. The main ducts 107 each have, in the non-inflated state, a width A. The longitudinal sides of the main ducts 107 which are turned away from one another are each delimited by a first series of first welded strips 113, which each have a length B, with first intermediate spaces 114 having a length C between them. At a distance D downstream from the outlet 111 of each main duct 107, a dividing weld 115 is provided. On each longitudinal side there are furthermore two ancillary ducts 108 and 109, which are separated from one another by in each case a row of spot welds 138. In use, air is blown into both main ducts 107 via connection 106. Air coming out of the outlet 111 of each main duct is divided into part-streams via the dividing welds 115. The ancillary ducts 108 and 109 are fed with air from the ends and also laterally via the intermediate spaces 114.

FIG. 8 shows the fourth embodiment, model 'half upper', which is denoted overall by reference numeral 151. It is composed of an inner sheet which is permeable to air and an outer sheet which is impermeable to air, both sheets being connected to one another by a peripheral weld 154 in order to define an air chamber between them, and two connections 156 are provided in the outer sheet for blowing in air. It has two main ducts 157, which run at an angle with respect to one another. Depending on the available space around the patient, the one or the other connection 156 will be used for blowing in air and the connection which is not used will be closed, as has been described for the embodiment from FIGS. 5-6. In that case, the main duct 157 which is in use and connected to the connection 156, will then serve as main duct.

In the embodiment according to FIG. 8, each main duct is delimited by two first welded strips 163, which are provided a distance C apart so as to leave an intermediate space 164 clear and each of which has in each case a different length B in this embodiment. The inlet 160 of the main duct has a width A at the connection 156. At a distance D from the outlet 161 of each main duct 157, a dividing weld 165 is provided.

In the embodiment according to FIG. 8, the first welded strips 163 of both main ducts which are furthest from the connection 156 together form a triangle which defines a corner of a triangular central configuration. The first welded strips 163 which are closest to the connection are each provided with a welded strip 189 which is connected to or at least adjoins welded strip 189, and in each case together form a different corner of said triangular configuration. The sides of this triangular configuration are in each case open so that an ancillary duct 158 is formed by said triangular configuration.

Downstream of the dividing weld 165 further welded strips 174, 186, 187 are provided which define further ducts 185, 188. On the other side of the air chamber, five spot welds 189 are provided which have the same function as the spot welds 25 in the embodiment from FIGS. 1-4 and the spot welds 81 in the embodiment from FIG. 6. In addition, reference numeral 190 also denotes welded strips.

In use, air is blown into the main duct 107 which is situated near connection 156 via one of the connections 156—the other one is closed. Air flowing out of the outlet 161 of this main duct is divided into part-streams by the dividing weld 165. The ancillary duct 158 is supplied with air from the end 191 which is situated near the connection in use and also laterally via the intermediate space 164.

In all the embodiments illustrated here, the sections of the inner sheet and outer sheet which are situated within the peripheral weld, viewed in the length and width direction of these sheets, have substantially equal dimensions (the thicknesses of the sheets can thus be different) and, in the non-inflated state, the inner and outer sheet lie substantially against one another by the sides which are turned towards one another.

In those instances where the term ancillary duct is used, this is in particular intended to mean a duct which, viewed in the transverse direction of the main duct, runs next to the main duct.

It will be clear that the above description has been given in order to illustrate the functioning of preferred embodiments of the invention and not in order to limit the scope of the invention. On the basis of the above explanation, many variations which fall within the spirit and scope of the present invention will be clear to a person skilled in the art.

LIST OF REFERENCE NUMERALS USED IN THE DRAWING

1=first embodiment
2=inner sheet
3=outer sheet
4=peripheral weld
5=air chamber
6=connection
7=main duct
8=first ancillary duct
9=second ancillary duct
10=inlet end
11=outlet end
12=first series
13=first welded strip
14=first intermediate space
15=dividing weld
16=transverse side of air chamber
17=transverse side of air chamber
18=longitudinal side of air chamber
19=longitudinal side of air chamber
20=further connecting weld, also referred to as first connecting weld
21=second series
22=second welded strip
23=second intermediate space
24=further connecting weld, also referred to as second connecting weld;
25=third connecting weld
35=further duct
51=second embodiment
52=inner sheet
53=outer sheet
54=peripheral weld
55=air chamber
56=connection
57=main duct
58=third ancillary duct
59=fourth ancillary duct
60=inlet end
61=outlet end
62=first series
63=first welded strip
64=first intermediate space
65=dividing weld
66=transverse side of air chamber
67=transverse side of air chamber
68=longitudinal side of air chamber
69=longitudinal side of air chamber
70=outer-bend welded strip
71=third series
72=third welded strip
73=third intermediate space
74=fourth series
75=fourth welded strip
76=fourth intermediate space
77=first end of first/fourth ancillary duct
78=further welded strip
79=mirror axis
80=longitudinal axis
81=fourth connecting weld
82=transverse side weld
83=further welded strip
84=further welded strip
85=further duct
100=person
101=third embodiment
104=peripheral weld
106=connection
107=main duct
108=ancillary duct
109=ancillary duct
110=inlet
111=outlet
113=first welded strip
114=first intermediate space
115=dividing weld
124=further welded strip
135=further duct
136=welded strip
137=spot weld
138=spot weld
151=fourth embodiment
154=peripheral weld
156=connection
157=main duct
158=ancillary duct
160=inlet
161=outlet
163=first welded strip
164=first intermediate space
165=dividing weld
174=further welded strip
185=further duct
186=further welded strip
187=further welded strip
188=further duct
189=welded strip
190=welded strip
A=main duct width (in the non-inflated state)
B=length of first welded strip
C=length of first intermediate space
D=distance from dividing weld to outlet end
E=length of first connecting weld
F=length of second intermediate space
G=width of first ancillary duct
H=length of second welded strip
I=length of second connecting weld
J=length of fourth intermediate space
X=width direction
Y=length direction

The invention claimed is:

1. Device for conveying air, in particular heated air, to a person,
in which the device comprises an air-permeable inner sheet to be turned towards the person and an air-impermeable outer sheet to be turned away from the person;
in which the inner sheet and the outer sheet are connected to one another in an air-tight manner by a peripheral weld which, together with the inner and outer sheet, defines an air chamber;

in which the device is provided with at least one connection for blowing in air;

in which the inner sheet and the outer sheet, in the air chamber, are connected to one another by a plurality of welds in such a manner that, when air is blown into the device via the connection, the former assumes a panel-like shape having a plurality of air ducts which are connected to one another;

in which the plurality of air ducts comprises a main duct and one or more ancillary ducts;

in which the main duct has an inlet end and an outlet end;

in which the connection ends at an inlet end of the main duct;

in that the main duct, viewed at the inlet end and in the non-inflated state, has a main duct width;

in that the plurality of welds comprises at least one first series of elongate first welded strips, first intermediate spaces between which are in line with one another, which first series delimits one side of the main duct;

in that the length of each of these first intermediate spaces, viewed in the non-inflated state, is in each case smaller than the main duct width;

in that the length of each first welded strip of the first series is at least 15% of the main duct width and at most 80% of the main duct width; and in that the plurality of welds comprises a dividing weld which is arranged outside of the main duct at the outlet end in line with the main duct and which is surrounded by divided air both upstream and downstream of the dividing weld.

2. Device according to claim 1, in which further welded strips are provided on that side of the dividing weld which, viewed in the direction of flow of the main duct, is downstream, and in which these further welded strips define one or more further ducts which extend to that end of the air chamber which is situated on said downstream side of the dividing weld.

3. Device according to claim 1, in which the distance from the dividing weld to the outside of the outlet end of the main duct is 50%-100% of the diameter of the main duct in the inflated state, said diameter of the main duct in the inflated state being defined as:

$$2 \times A/\pi,$$

with A=the main duct width in the non-inflated state.

4. Device according to claim 1, in which the length of each first welded strip of the first series is at least 20% of the main duct width.

5. Device according to claim 1, in which the length of each first welded strip of the first series is at most 70%, such as at most 60%, of the main duct width.

6. Device according to claim 1, in which the length of each of the first intermediate spaces between the first welded strips of the first series is at most 80% of the main duct width, preferably at most 75% of the main duct width, more preferably at most 70% of the main duct width.

7. Device according to claim 1, in which the length of each of the first intermediate spaces between the first welded strips of the first series is at least 50% of the main duct width, preferably at least 60% of the main duct width.

8. Device according to claim 1, in which
the air chamber has an elongate shape;
in which the connection is provided at a transverse side of the elongate air chamber, in the centre thereof;
in which the main duct is a straight duct which is delimited on both sides by said first series of first welded strips; and
in which at least one first ancillary duct runs on either side of the main duct and parallel to the main duct.

9. Device according to claim 8, in which the first welded strips of the first series in each case are of an approximately equal length and in which the first intermediate spaces in each case have an approximately equal length.

10. Device according to claim 2,
in which the air chamber has an elongate shape;
in which the connection is provided at a transverse side of the elongate air chamber, in the centre thereof;
in which the main duct is a straight duct which is delimited on both sides by said first series of first welded strips;
in which at least one first ancillary duct runs on either side of the main duct and parallel to the main duct; and
in which the further welded strips, at the outlet end, have an elongate first connecting weld in line with each first series and at a distance thereto, which first connecting welds, viewed in the direction of flow of the main duct, diverge from one another and have a length which is longer than the length of the first welded strips of the first series.

11. Device according to claim 8,
in which a second ancillary duct extends along that side of each first ancillary duct which is turned away from the main duct; and
in which the plurality of welds comprises a second series of elongate second welded strips on each side of the main duct which are in line with second intermediate spaces and form the partition between the first and second ancillary duct; and
in which the length of each of these second intermediate spaces, viewed in the non-inflated state, is in each case greater than the length of the first intermediate spaces.

12. Device according to claim 11, in which, viewed in the non-inflated state, the length of the second intermediate spaces is greater than 80%, in particular greater than 90%, of the width of the first ancillary duct.

13. Device according to claim 11, in which the length of each second welded strip of the second series is 30% to 70%, such as 40% to 60%, of the length of the first welded strips of the first series.

14. Device according to claim 11, in which the second welded strips of the second series in each case are of approximately equal length and in which the second intermediate spaces in each case are of approximately equal length.

15. Device according to claim 2,
in which the air chamber has an elongate shape;
in which the connection is provided at a transverse side of the elongate air chamber, in the centre thereof;
in which the main duct is a straight duct which is delimited on both sides by said first series of first welded strips;
in which at least one first ancillary duct runs on either side of the main duct and parallel to the main duct;
in which a second ancillary duct extends along that side of each first ancillary duct which is turned away from the main duct;
in which the plurality of welds comprises a second series of elongate second welded strips on each side of the main duct which are in line with second intermediate spaces and form the partition between the first and second ancillary duct;
in which the length of each of these second intermediate spaces, viewed in the non-inflated state, is in each case greater than the length of the first intermediate spaces; and
in which the further welded strips, at the outlet end, in line with each second series and at a distance therefrom comprise an elongate second connecting weld, which second connecting welds, viewed in the direction of flow of the main duct, diverge from one another and have a length which is greater than that of the first welded strips of the first series.

16. Device according to claim 15, in which the plurality of welds, at the inlet end, in line with each first and second series comprises a third connecting weld, which is in particular pointed.

17. Device according to claim 1, in which the air chamber has an elongate shape;
in which the connection is provided on a longitudinal side of the elongate air chamber;
in which the main duct is a curved duct which extends from the connection to the centre of said air chamber, viewed in the width direction of the elongate air chamber;
in which the first series delimits the inner-bend side of the main duct; in which a third ancillary duct extends on the outer-bend side of the main duct which is substantially straight and extends in the longitudinal direction of the elongate air chamber;
in which the plurality of welds comprises a third series of elongate third welded strips which are in line with third intermediate spaces, which third series delimits that side of the third ancillary duct which is adjacent to the main duct; and
in which the plurality of welds comprises one or more elongate outer-bend welded strips which are directed obliquely towards the third series in order, together with one or more third welded strips of the third series which are situated downstream of the outer-bend welded strips, to form the outer bend of the main duct.

18. Device according to claim 17, in which a fourth ancillary duct extends on that side of the third ancillary duct which is turned away from the main duct, and extends parallel to the third ancillary duct; in which the plurality of welds comprises a fourth series of elongate fourth welded strips which are in line with fourth intermediate spaces, which fourth series forms the boundary between the third and fourth ancillary ducts; in which the length of each of these fourth intermediate spaces, viewed in the non-inflated state, is in each case greater than the length of the first intermediate spaces.

19. Device according to claim 17, in which the one or more ancillary ducts have a first end and in which, viewed in the transverse direction of the elongate air chamber, these first ends are situated substantially next to the inlet end of the main duct; and in which, viewed in the longitudinal direction of the elongate air chamber, the plurality of welds upstream of the inlet end comprises one or more fourth connecting welds.

20. Device according to claim 17, in which the elongate air chamber, viewed in the longitudinal direction thereof, has a longitudinal centre and is mirror-symmetrical with respect to a mirror axis which is at right angles to the longitudinal axis of the elongate air chamber and crosses this longitudinal centre.

21. Device according to claim 20, in which the connections are provided at approximately one quarter and three quarters of the length of the elongate air chamber.

22. Device according to claim 1, in which the inner sheet has a permeability to air of <300 mm/sec, in particular <200 mm/sec, measured according to ISO 9237:1995(E).

23. Device according to claim 1, in which the sections of the inner sheet and outer sheet which are situated inside the peripheral weld, viewed in the length and which the inner sheet and outer sheet, viewed in the non-inflated state, substantially lie against one another by those sides of said inner sheet and said outer sheet which are turned towards one another.

* * * * *